United States Patent
Jordan et al.

(10) Patent No.: US 8,057,527 B2
(45) Date of Patent: Nov. 15, 2011

(54) ENDOPROSTHESIS HOLDER

(75) Inventors: Gary Jordan, Litchfield, NH (US); F. Anthony Headley, Jr., Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 423 days.

(21) Appl. No.: 12/188,692

(22) Filed: Aug. 8, 2008

(65) Prior Publication Data

US 2009/0048653 A1    Feb. 19, 2009

Related U.S. Application Data

(60) Provisional application No. 60/964,068, filed on Aug. 9, 2007.

(51) Int. Cl.
*A61F 2/84* (2006.01)
(52) U.S. Cl. ........................ 623/1.11; 606/108
(58) Field of Classification Search ................. 606/108; 623/1.11, 1.12, 1.23
See application file for complete search history.

(56) References Cited

U.S. PATENT DOCUMENTS

| | | | |
|---|---|---|---|
| 5,733,925 A | 3/1998 | Kunz et al. | |
| 5,833,632 A | 11/1998 | Jacobsen et al. | |
| 6,014,919 A | 1/2000 | Jacobsen et al. | |
| 6,120,522 A | 9/2000 | Vrba et al. | |
| 6,260,458 B1 | 7/2001 | Jacobsen et al. | |
| 6,428,489 B1 * | 8/2002 | Jacobsen et al. | 600/585 |
| 6,431,039 B1 | 8/2002 | Jacobsen et al. | |
| 6,607,551 B1 * | 8/2003 | Sullivan et al. | 623/1.11 |
| 7,011,675 B2 | 3/2006 | Hemerick et al. | |
| 7,208,002 B2 | 4/2007 | Shelso | |
| 2002/0035396 A1 | 3/2002 | Heath | |
| 2006/0178732 A1 | 8/2006 | Chobotov et al. | |
| 2008/0009934 A1 | 1/2008 | Schneider et al. | |

FOREIGN PATENT DOCUMENTS

| | | |
|---|---|---|
| EP | 1 656 963 | 5/2006 |
| WO | WO 00/71058 | 11/2000 |
| WO | WO 01/87180 | 11/2001 |

OTHER PUBLICATIONS

PCT Notification of Transmittal of the International Search Report and the Written Opinion of the International Searching Authority, or the Declaration for International Application No. PCT/US2008/072622, Oct. 30, 2008 (3 pages).
PCT International Search Report for International Application No. PCT/US2008/072622, Oct. 30, 2008 (5 pages).
PCT Written Opinion of the International Searching Authority for International Application No. PCT/US2008/072622, Oct. 30, 2008 (7 pages).

* cited by examiner

*Primary Examiner* — Ryan Severson
(74) *Attorney, Agent, or Firm* — Vidas, Arrett & Steinkraus, P.A.

(57) ABSTRACT

An endoprosthesis holder includes a proximal connector structure having an outer surface. A distal connector structure has an outer surface. An intermediate connector structure is connected to the proximal and distal connector structures such that the intermediate connector structure is between the proximal and distal connector structures. The intermediate connector structure includes one or more intermediate transverse structures and one or more axial structures. The one or more intermediate transverse structures are connected to one another and to the proximal and distal connector structures by the one or more axial structures. The intermediate connector structure has an outer surface. An outward protrusion is connected to one or more of the outer surfaces of the proximal connector structure or distal connector structure or intermediate connector structure.

11 Claims, 2 Drawing Sheets

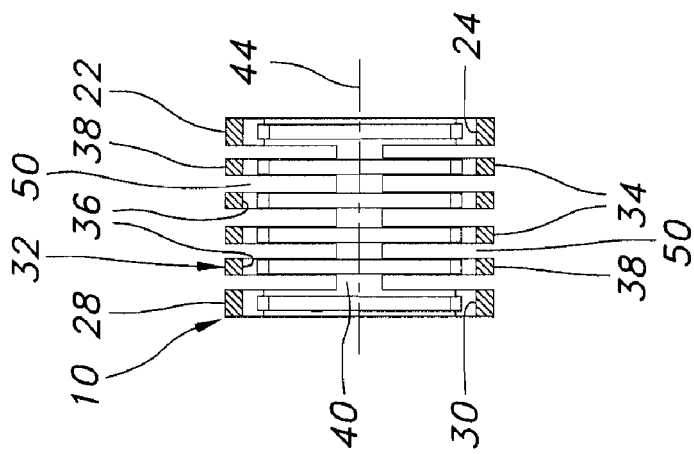
FIG. 3
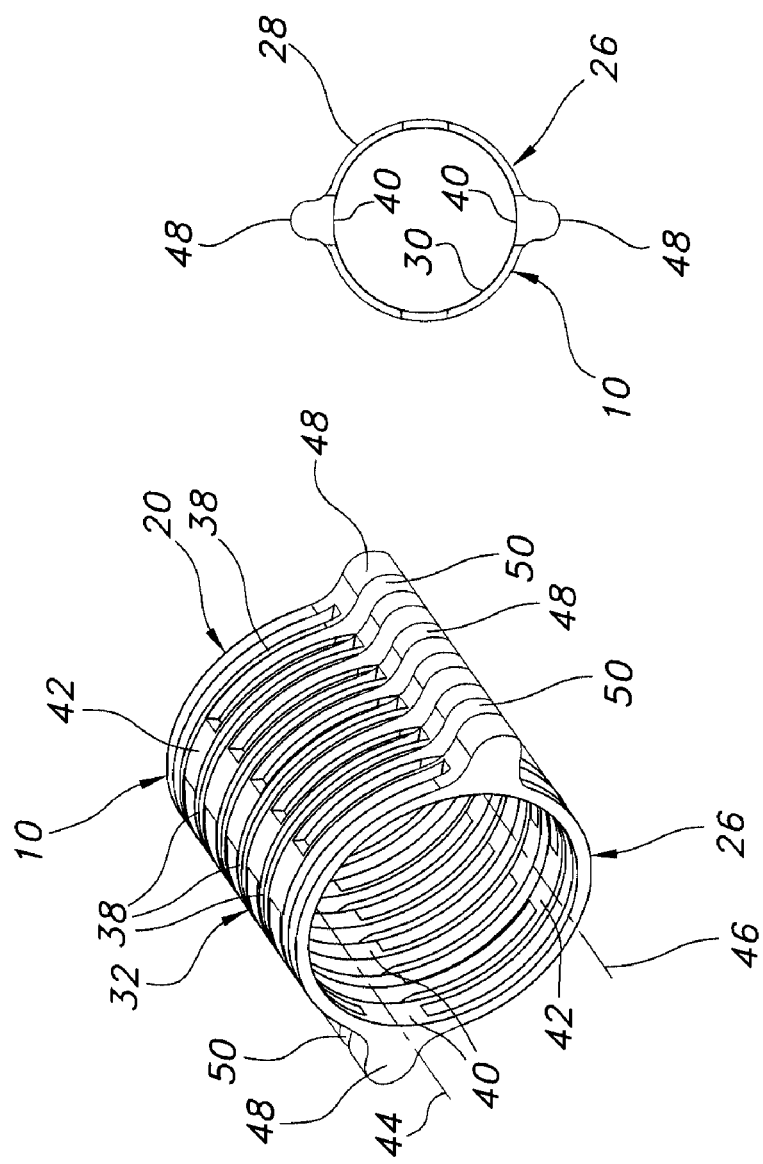
FIG. 4
FIG. 2

ENDOPROSTHESIS HOLDER

CROSS-REFERENCE TO RELATED APPLICATION

This patent application claims priority to and the benefit of U.S. Provisional Patent Application No. 60/964,068 filed Aug. 9, 2007 which is hereby incorporated by reference herein.

FIELD OF THE INVENTION

The present invention relates generally to endoprosthesis holders and, more specifically, to an endoprosthesis holder having increased flexibility and a substantial torsional stiffness.

BACKGROUND OF THE INVENTION

An endoprosthesis or intraluminal prosthesis is a medical device used in the treatment of diseased bodily lumens. One type of endoprosthesis used in the repair and/or treatment of diseases in various body vessels is a stent. A stent is a generally longitudinal tubular device formed of biocompatible material which is useful to open and support various lumens in the body. For example, stents may be used in the vascular system, urogenital tract, esophageal tract, tracheal/bronchial tubes and bile duct, as well as in a variety of other applications in the body. These devices are implanted within the vessel to open and/or reinforce collapsing or partially occluded sections of the lumen.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Tubular shaped structures, which have been used as intraluminal vascular stents, have included helically wound coils which may have undulations or zig-zags therein, slotted stents, ring stents, braided stents and open mesh wire stents. Super-elastic materials and metallic shape memory materials have also been used to form stents.

A stent may be delivered to a specific location within a body lumen by a delivery system. The delivery system includes an elongate inner structure on which an endoprosthesis holder is supported. The elongate inner structure may be cylindrical. The endoprosthesis holder may be tubular and supported on the elongate inner structure in coaxial relation therewith. A tubular stent is supported on the endoprosthesis holder. If the endoprosthesis holder is tubular, the stent is supported in coaxial relation therewith. A tubular sheath covers the stent in coaxial relation therewith and with the elongate inner structure. The endoprosthesis holder is fixed to the elongate inner structure to prevent axial displacement of the endoprosthesis holder relative to the elongate inner structure. The endoprosthesis holder engages the stent to prevent axial displacement of the stent relative to the endoprosthesis holder. This retention of the stent by the endoprosthesis holder maintains the axial position of the stent relative to the endoprosthesis holder and elongate inner structure when the sheath is axially displaced relative to the elongate inner structure and endoprosthesis holder. Without the retention of the stent provided by the endoprosthesis holder, axial displacement of the sheath relative to the elongate inner structure may cause associated axial displacement of the stent as a result of frictional contact between the sheath and stent.

The retention of the stent by the endoprosthesis holder is beneficial during deployment of the stent by providing for the longitudinal position of the stent within the bodily lumen to be maintained during relative axial displacement of the sheath. The longitudinal position of the stent within the bodily lumen is typically significant. The maintenance of the longitudinal position of the stent relative to the elongate inner structure may be particularly difficult during reconstrainment. The sheath may be longitudinally retracted relative to the elongate inner structure such that a distal axial portion of the stent is exposed by the sheath and a proximal axial portion of the stent remains covered by the sheath. Reconstrainment refers to the forward axial displacement of the sheath relative to the elongate inner structure such that the axial distal portion of the stent which was uncovered by the longitudinal retraction of the sheath is recovered partially or completely by the sheath. The forward axial displacement of the sheath may cause forward longitudinal displacement of the stent relative to the elongate inner structure and, typically, the bodily lumen as a result of contact between the sheath and stent. Accordingly, the stent may be carried by the sheath. Limiting or completely preventing such forward displacement of the stent relative to the elongate inner structure and bodily lumen is typically advantageous.

Stents frequently are required to be delivered through bodily lumens which are curved and tortuous. Typically, it is desirable for the endoprosthesis holder, stent, sheath, and elongate inner structure to have sufficient flexibility to conform to the curved and tortuous sections of the bodily lumen during delivery of the stent therethrough. Such conformance by the endoprosthesis holder normally requires the endoprosthesis holder to be flexible to resist kinking thereof. Also, it is desirable for the endoprosthesis holder to be torsionally stiff.

SUMMARY OF THE INVENTION

The endoprosthesis holder of the present invention includes proximal and distal connector structures having respective outer surfaces. An intermediate connector structure is connected to the proximal and distal connector structures such that the intermediate connector structure is between the proximal and distal connector structures. The intermediate connector structure includes one or more intermediate transverse structures and one or more axial structures. The one or more intermediate transverse structures are connected to one another and to the proximal and distal connector structures by the one or more axial structures. The intermediate connector structure has an outer surface. An outward protrusion is connected to one or more of the outer surfaces of the proximal connector structure or distal connector structure or intermediate connector structure.

The outward protrusion engages the stent when the endoprosthesis holder is located within the stent. The engagement of the outward protrusion with the stent resists axial displacement of the stent relative to the endoprosthesis holder. Consequently, when the endoprosthesis holder is fixed to the elongate inner structure, axial displacement of the stent relative to the elongate inner structure is obstructed. This retains the axial position of the stent relative to the elongate inner structure. This retention of the stent is maintained when the stent is located within a sheath and the sheath is axially displaced relative to the elongate inner structure. As a result, the endoprosthesis holder and the fixed connection thereof to the elongate inner structure maintains the longitudinal position of the stent within the bodily lumen during reconstrainment.

The connection of the one or more intermediate transverse structures to one another and to the proximal and distal connector structures by the one or more axial structures provides flexibility to the endoprosthesis holder. This flexibility facilitates conformance of the endoprosthesis holder to curved and tortuous bodily lumens through which the endoprosthesis holder and associated stent and delivery system may be deployed. This flexibility resists kinking of the endoprosthesis holder, stent, and associated delivery system. Also, the connections of the intermediate transverse structures which are provided by the axial structures provide torsional stiffness to the endoprosthesis holder.

These and other features of the invention will be more fully understood from the following description of specific embodiments of the invention taken together with the accompanying drawings.

BRIEF DESCRIPTION OF THE DRAWINGS

In the drawings:

FIG. 2 is a perspective view of the endoprosthesis holder of FIG. 1, the endoprosthesis holder being transversely rotated 90 degrees relative to the orientation of FIG. 1;

FIG. 3 is a longitudinal cross-sectional view of the endoprosthesis holder of FIG. 2; and FIG. 4 is a left end elevational view of the endoprosthesis holder of FIG. 1.

Corresponding reference characters indicate corresponding parts throughout the several views of the drawings.

DETAILED DESCRIPTION OF THE INVENTION

Figure 1:
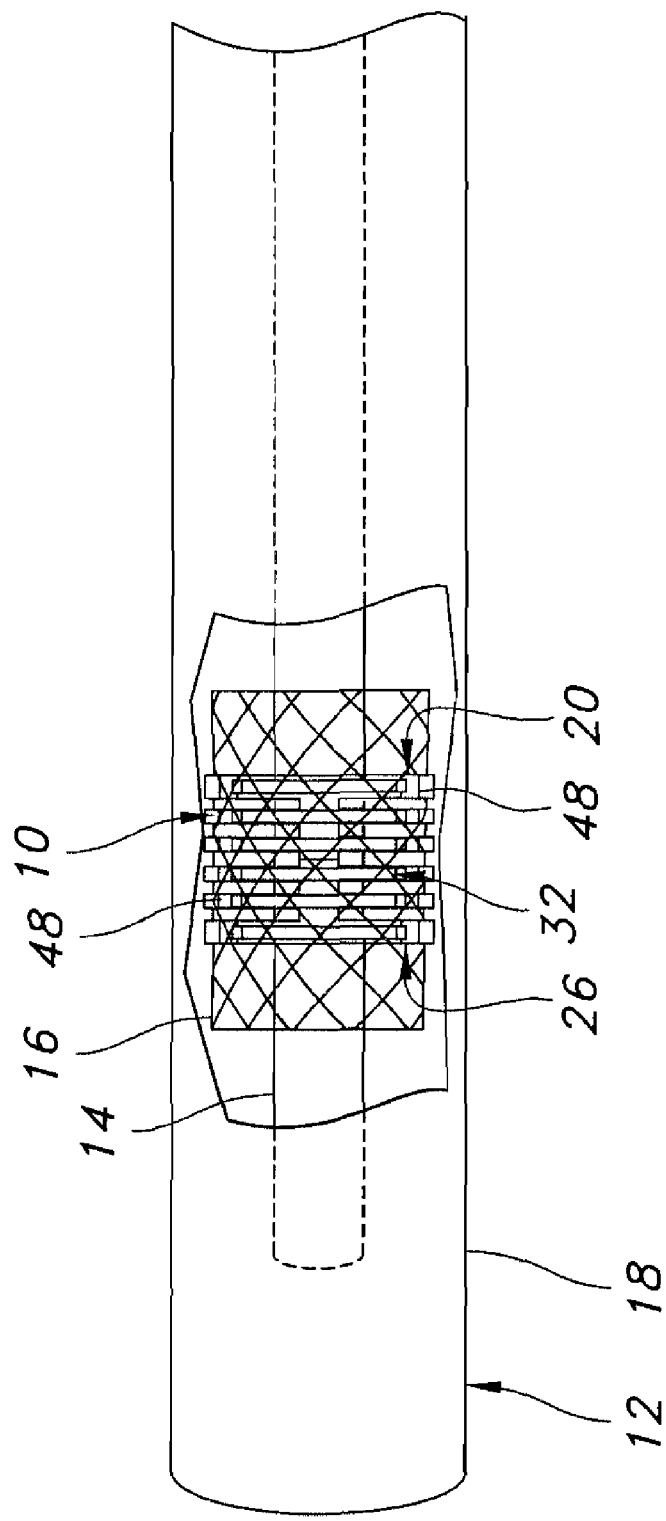
FIG. 1 is a longitudinal cross-sectional view of the endoprosthesis holder of the present invention showing the endoprosthesis holder located within a stent, the stent being shown as located within a sheath, the endoprosthesis holder being shown as fixed to an elongate inner structure located within the endoprosthesis holder.

Referring to the drawings and more specifically to FIG. 1, the endoprosthesis or stent holder 10 is used with a delivery system 12. The delivery system 12 includes an elongate inner structure 14 on which the endoprosthesis holder 10 is mounted in coaxial relation therewith. The mounting of the endoprosthesis holder 10 on the inner structure 14 provides for the obstruction of axial displacement of the endoprosthesis holder relative to the inner structure. The mounting of the endoprosthesis holder 10 on the inner structure 14 may further provide for the obstruction transverse or rotational displacement of the endoprosthesis holder relative to the inner structure.

A stent 16 is located around the endoprosthesis holder 10 in coaxial relation therewith. The stent 16 is engaged by radial outward protrusions 48 of the endoprosthesis holder 10 such that axial displacement of the stent 16 relative to the endoprosthesis holder is obstructed. The engagement of the stent 16 by the outward protrusions 48 may further obstruct transverse or rotational displacement of the stent relative to the endoprosthesis holder. The delivery system 12 includes a tubular sheath 18 which is located around the stent 16 in coaxially relation therewith.

The delivery system 12 provides for the deployment of the stent 16 to a location within a body lumen by positioning the stent 16 around and in engagement with the endoprosthesis holder 10 such that axial displacement of the stent 16 relative to the endoprosthesis holder 10 is obstructed. The sheath 18 is located around the stent 16 such that the stent is covered completely in the axial direction by the sheath.

The portion of the delivery system 12 in which the stent 16 is contained is inserted into the body lumen and displaced relative thereto to position the stent at the desired location within the body lumen. When the delivery system 12 has positioned the stent at the desired location within the body lumen, the sheath 18 is retracted to uncover the stent 16 in the longitudinal direction. During the retraction of the sheath 18, the stent 16 maintains the axial position thereof relative to the inner structure 14 by the engagement of the stent by the outward protrusions 48 of the endoprosthesis holder 10. The engagement between the outward protrusions 48 and the stent 16 resists the stent from being carried by the sheath 18 in the direction of the retraction thereof. During the retraction of the sheath 18, it may be desired to cease the retraction and return the sheath to an axial position in which all or part of the stent 16 which was uncovered during the retraction of the sheath is re-covered by the sheath. This is typically accomplished by axial displacement of the sheath 18 relative to the inner structure 14 in a direction which opposes the direction of the retraction of the sheath. This axial displacement of the sheath 18 relative to the inner structure 14 such that the sheath covers a portion of the stent which was previously covered by the sheath is referred to as reconstrainment. During the reconstrainment, the axial position of the stent 16 relative to the endoprosthesis holder 10 and inner structure 14 is maintained by the engagement of the stent by the outward protrusions 48. The engagement between the outward protrusions 48 and stent 16 obstructs the stent from being carried by the sheath 18. The carrying of the stent 16 by the sheath 18 would typically result in the stent 16 being axially displaced relative to the inner structure 14 in the direction of the reconstrainment of the sheath 18. Reconstrainment may be desired as a result of a determination that further displacement of the delivery system 12 within the body lumen is necessary to position the stent 16 at a different location within the body lumen.

The endoprosthesis holder 10 includes a proximal connector structure 20 having outer and inner surfaces 22, 24. A distal connector structure 26 has outer and inner surfaces 28, 30. The proximal and distal connector structures 20, 26 have annular cross-sections.

The endoprosthesis holder 10 includes an intermediate connector structure 32 which is integrally connected to the proximal and distal connector structures 20, 26 such that the intermediate connector structure is between the proximal and distal connector structures and in coaxial relation therewith. The intermediate connector structure 32 has an annular cross-section, the dimensions of which are generally the same as the dimensions of the annular cross-sections of the proximal and distal connector structures 20, 26. The intermediate connector structure 32 has an outer surface 34 which is contiguous with the outer surfaces 22, 28 of the proximal and distal connector structures 20, 26. The intermediate connector structure 32 has an inner surface 36 which is contiguous with the inner surfaces 24, 30 of the proximal and distal connector structures 20, 26.

The intermediate connector structure 32 includes intermediate transverse structures 38 each of which has an annular cross section. The intermediate transverse structures 38 are aligned longitudinally in coaxial relation to one another. The intermediate transverse structures 38 each have two pairs of axial structures 40, 42 integrally connected thereto. Each pair of axial structures 40 are connected to diametrically opposed locations of the corresponding intermediate transverse structure 38. Each of the pairs of axial structures 40, 42 extend in opposite axial directions from the intermediate transverse structure 38 to which both of the pairs of axial structures 40, 42 are integrally connected.

The axial structures 40, 42 have respective axial center lines 44, 46. The axial center lines 44 of the axial structures 40 are circumferentially offset by 90 degrees relative to the axial center lines 46 of the axial structures 42 which are connected to the same intermediate transverse structure.

The intermediate transverse structures 38 which are adjacent to the proximal and distal connector structures 20, 26 are integrally connected thereto by corresponding pairs of the axial structures 40.

The endoprosthesis holder 10 includes outward protrusions 48 which are integrally connected to the outer surfaces 22, 28, 34 of the proximal, distal, and intermediate connector structures 20, 26, 32. The outward protrusions 48 are lobe-shaped and have diametrically opposed locations on the outer surfaces 22, 28, 34 of the proximal, distal, and intermediate connector structures 20, 26, 32.

The outward protrusions 48 are connected to sections of the outer surface 34 of the intermediate connector structure 32 which are defined by one set of the axial structures 40 which are diametrically opposed to one another. The outward protrusions 48 extending from the axial structures 40 which are connected to the proximal and distal connector structures 20, 26 extend to the proximal and distal connector structures 20, 26 for integral connection to the outer surfaces 22, 28.

The connection of the outward protrusions 48 to the axial structures 40 and proximal and distal connectors structures 20, 26 provides for the outward protrusions 48 to be arranged in diametrically opposed rows. The circumferential offset between the axial structures 40 and axial structures 44 provides for axial clearances 50 between the outward protrusions 48.

The endoprosthesis holder 10 may be formed of expanded polytetrafluoroethylene (ePTFE) or polyurethane. The endoprosthesis holder 10 may be formed of biocompatible materials, such as biocompatible polymers including those which are known. Such polymers may include fillers such as metals, carbon fibers, glass fibers or ceramics. Also, such polymers may include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in the endoprosthesis holder 10. In alternative embodiments, the endoprosthesis holder 10 may be formed from a polymer sleeve.

The endoprosthesis holder 10 may be formed of materials such as nitinol, Elgiloy, stainless steel, cobalt chromium, including MP35N, cobalt-based alloy, tantalum, niobium, platinum, gold, titanium, combinations thereof and other biocompatible metals, polymers and materials. Additionally, the endoprosthesis holder 10 may include structural members which have an inner core formed of tantalum, gold, platinum, iridium, or a combination thereof, and an outer cladding of nitinol to provide composite members for improved radio-opacity or visibility. Examples of such composite members are disclosed in U.S. Patent Application Publication No. 2002/0035396 which is hereby incorporated by reference herein.

The endoprosthesis holder 10 maybe treated with anti-thrombogenic agents (such as heparin, heparin derivatives, urokinase, and PPack (dextrophenylalanine proline arginine chloromethylketone)), anti-proliferative agents (such as enoxaprin, angiopeptin, or monoclonal antibodies capable of blocking smooth muscle cell proliferation, hirudin, and acetylsalicylic acid), anti-inflammatory agents (such as dexamethasone, prednisolone, corticosterone, budesonide, estrogen, sulfasalazine, and mesalamine), antineoplastic/antiproliferative/anti-miotic agents (such as paclitaxel, 5-fluorouracil, cisplatin, vinblastine, vincristine, epothilones, endostatin, angiostatin and thymidine kinase inhibitors), anesthetic agents (such as lidocaine, bupivacaine, and ropivacaine), anti-coagulants (such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides), vascular cell growth promotors (such as growth factor inhibitors, growth factor receptor antagonists, transcriptional activators, and translational promotors), vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin), cholesterol-lowering agents, vasodilating agents, and agents which interfere with endogenous vascoactive mechanisms.

The endoprosthesis holder 10 is secured to the inner structure 14 of the delivery system 12 such that the endoprosthesis holder is located around the inner structure in coaxial relation therewith. The securing of the endoprosthesis holder 10 to the inner structure 14 obstructs axial displacement of the endoprosthesis holder relative to the inner structure. The securing of the endoprosthesis holder 10 to the inner structure 14 may further provide for obstruction of transverse or rotational displacement of the endoprosthesis holder relative to the inner structure.

The stent 16 is located around the endoprosthesis holder 10 in coaxial relation therewith. The stent 16 has one or more voids in which the outward protrusions 48 extend to obstruct axial displacement of the stent 16 relative to the endoprosthesis holder 10. Consequently, axial displacement of the stent 16 relative to the inner structure 14 is obstructed. The sheath 18 of the delivery system 12 is located around the stent 16 in coaxial relation therewith.

During longitudinal displacement of the sheath 18 relative to the inner structure 14, possible longitudinal displacement of the stent 16 associated with the sheath is resisted by the outward protrusions 48 which extend into the one or more voids in the stent 16. Consequently, the axial position of the stent 16 relative to the inner structure 14 is maintained such that longitudinal retraction of the sheath 18 relative to the inner structure 14 may provide for the uncovering of an axial portion or all of the outer surface of the stent 16 which was previously covered by the sheath. Also, the maintenance of the axial position of the stent 16 relative to the inner structure 14 which is provided by the extension of the outward protrusions 48 into the one or more voids in the stent results in forward longitudinal displacement of the sheath 18 relative to the inner structure 14 enabling the sheath to cover an axial portion of the stent or the entire stent. This re-covering of the stent 16 by the sheath 18 provides reconstrainment of the stent.

Stent 16 may be treated with a therapeutic agent or agents. "Therapeutic agents", "pharmaceuticals," "pharmaceutically active agents", "drugs" and other related terms may be used interchangeably herein and include genetic therapeutic agents, non-genetic therapeutic agents and cells. Therapeutic agents may be used singly or in combination. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Non-limiting examples of useful therapeutic agents include, but are not limited to, adrenergic agents, adrenocortical steroids, adrenocortical suppressants, alcohol deterrents, aldosterone antagonists, amino acids and proteins, ammonia detoxicants, anabolic agents, analeptic agents, analgesic agents, androgenic agents, anesthetic agents, anorectic compounds, anorexic agents, antagonists, anterior pituitary activators and suppressants, anthelmintic agents, anti-adrenergic agents, anti-allergic agents, anti-amebic agents, anti-androgen agents, anti-anemic agents, anti-anginal agents, anti-anxiety agents, anti-arthritic agents, anti-asthmatic agents, anti-atherosclerotic agents, antibacterial agents, anticholelithic agents, anticholelithogenic agents, anticholinergic agents, anticoagulants, anticoccidal agents, anticonvulsants, antidepressants, antidiabetic agents, antidiuretics, antidotes, antidyskinetics agents, anti-emetic agents, anti-epileptic agents, anti-estrogen agents, antifibrinolytic agents, antifungal agents, antiglaucoma agents, antihemophilic agents, antihemophilic Factor, antihemorrhagic agents, antihistaminic agents, antihyperlipidemic agents, antihyperlipoproteinemic agents, antihypertensives, antihypotensives, anti-infective agents, anti-inflammatory agents, antikeratinizing agents, antimicrobial agents, antimigraine agents, antimitotic agents, antimycotic agents, antineoplastic agents, anti-cancer supplementary potentiating agents, antineutropenic agents, antiobsessional agents, antiparasitic agents, antiparkinsonian drugs, antipneumocystic agents, antiproliferative agents, antiprostatic hypertrophydrugs, antiprotozoal agents, antipruritics, antipsoriatic agents, antipsychotics, antirheumatic agents, antischistosomal agents, antiseborrheic agents, antispasmodic agents, antithrombotic agents, antitussive agents, anti-ulcerative agents, anti-urolithic agents, antiviral agents, benign prostatic hyperplasia therapy agents, blood glucose regulators, bone resorption inhibitors, bronchodilators, carbonic anhydrase inhibitors, cardiac depressants, cardioprotectants, cardiotonic agents, cardiovascular agents, choleretic agents, cholinergic agents, cholinergic agonists, cholinesterase deactivators, coccidiostat agents, cognition adjuvants and cognition enhancers, depressants, diagnostic aids, diuretics, dopaminergic agents, ectoparasiticides, emetic agents, enzyme inhibitors, estrogens, fibrinolytic agents, free oxygen radical scavengers, gastrointestinal motility agents, glucocorticoids, gonad-stimulating principles, hemostatic agents, histamine H2 receptor antagonists, hormones, hypocholesterolemic agents, hypoglycemic agents, hypolipidemic agents, hypotensive agents, HMGCoA reductase inhibitors, immunizing agents, immunomodulators, immunoregulators, immunostimulants, immunosuppressants, impotence therapy adjuncts, keratolytic agents, LHRH agonists, luteolysin agents, mucolytics, mucosal protective agents, mydriatic agents, nasal decongestants, neuroleptic agents, neuromuscular blocking agents, neuroprotective agents, NMDA antagonists, non-hormonal sterol derivatives, oxytocic agents, plasminogen activators, platelet activating factor antagonists, platelet aggregation inhibitors, post-stroke and post-head trauma treatments, progestins, prostaglandins, prostate growth inhibitors, prothyrotropin agents, psychotropic agents, radioactive agents, repartitioning agents, scabicides, sclerosing agents, sedatives, sedative-hypnotic agents, selective adenosine A1 antagonists, adenosine A2 receptor antagonists (e.g., CGS 21680, regadenoson, UK 432097 or GW 328267), serotonin antagonists, serotonin inhibitors, serotonin receptor antagonists, steroids, stimulants, thyroid hormones, thyroid inhibitors, thyromimetic agents, tranquilizers, unstable angina agents, uricosuric agents, vasoconstrictors, vasodilators, vulnerary agents, wound healing agents, xanthine oxidase inhibitors, and the like, and combinations thereof Useful non-genetic therapeutic agents for use in connection with the present invention include, but are not limited to,
(a) anti-thrombotic agents such as heparin, heparin derivatives, urokinase, clopidogrel, and PPack (dextrophenylalanine proline arginine chloromethylketone);
(b) anti-inflammatory agents such as dexamethasone, prednisolone, corticosterone, budesonide, estrogen, sulfasalazine and mesalamine;
(c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors;
(d) anesthetic agents such as lidocaine, bupivacaine and ropivacaine;
(e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides;
(f) vascular cell growth promoters such as growth factors, transcriptional activators, and translational promotors;
(g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;
(h) protein kinase and tyrosine kinase inhibitors (e.g., tyrphostins, genistein, quinoxalines);
(i) prostacyclin analogs;
(j) cholesterol-lowering agents;
(k) angiopoietins;
(l) antimicrobial agents such as triclosan, cephalosporins, aminoglycosides and nitrofurantoin;
(m) cytotoxic agents, cytostatic agents and cell proliferation affectors;
(n) vasodilating agents;
(o) agents that interfere with endogenous vasoactive mechanisms;
(p) inhibitors of leukocyte recruitment, such as monoclonal antibodies;
(q) cytokines;
(r) hormones;
(s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin;

(t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine);

(u) bARKct inhibitors;

(v) phospholamban inhibitors;

(w) Serca 2 gene/protein;

(x) immune response modifiers including aminoquizolines, for instance, imidazoquinolines such as resiquimod and imiquimod;

(y) human apolioproteins (e.g., AI, AII, AIII, AIV, AV, etc.);

(z) selective estrogen receptor modulators (SERMs) such as raloxifene, lasofoxifene, arzoxifene, miproxifene, ospemifene, PKS 3741, MF 101 and SR 16234;

(aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar;

(bb) prostaglandin E agonists, including PGE2 agonists, such as alprostadil or ONO 8815Ly;

(cc) thrombin receptor activating peptide (TRAP);

(dd) vasopeptidase inhibitors including benazepril, fosinopril, lisinopril, quinapril, ramipril, imidapril, delapril, moexipril and spirapril;

(ee) thymosin beta 4;

(ff) phospholipids including phosphorylcholine, phosphatidylinositol and phosphatidylcholine; and (gg) VLA-4 antagonists and VCAM-1 antagonists.

The non-genetic therapeutic agents may be used individually or in combination, including in combination with any of the agents described herein.

Further examples of non-genetic therapeutic agents, not necessarily exclusive of those listed above, include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Useful genetic therapeutic agents for use in connection with the present invention include, but are not limited to, anti-sense DNA and RNA as well as DNA coding for the various proteins (as well as the proteins themselves), such as (a) anti-sense RNA; (b) tRNA or rRNA to replace defective or deficient endogenous molecules; (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor; (d) cell cycle inhibitors including CD inhibitors, and (e) thymidine kinase ("TK") and other agents useful for interfering with cell proliferation. DNA encoding for the family of bone morphogenic proteins ("BMP's") are also useful and include, but not limited to, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently desirably BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include, but not limited to, viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SUPRATEK), lipids such as cationic lipids, liposomes, lipoplexes, nanoparticles, or microparticles, with and without targeting sequences such as the protein transduction domain (PTD).

Cells for use in connection with the present invention may include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following:

(a) Ca-channel blockers including benzothiazapines such as diltiazem and clentiazem, dihydropyridines such as nifedipine, amlodipine and nicardapine, and phenylalkylamines such as verapamil;

(b) serotonin pathway modulators including: 5-HT antagonists such as ketanserin and naftidrofuryl, as well as 5-HT uptake inhibitors such as fluoxetine;

(c) cyclic nucleotide pathway agents including phosphodiesterase inhibitors such as cilostazole and dipyridamole, adenylate/Guanylate cyclase stimulants such as forskolin, as well as adenosine analogs;

(d) catecholamine modulators including α-antagonists such as prazosin and bunazosine, β-antagonists such as propranolol and α/β-antagonists such as labetalol and carvedilol;

(e) endothelin receptor antagonists such as bosentan, sitaxsentan sodium, atrasentan, endonentan;

(f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine;

(g) Angiotensin Converting Enzyme (ACE) inhibitors such as cilazapril, fosinopril and enalapril;

(h) ATII-receptor antagonists such as saralasin and losartin;

(i) platelet adhesion inhibitors such as albumin and polyethylene oxide;

(j) platelet aggregation inhibitors including cilostazole, aspirin and thienopyridine (ticlopidine, clopidogrel) and GP IIb/IIIa inhibitors such as abciximab, epitifibatide and tirofiban;

(k) coagulation pathway modulators including heparinoids such as heparin, low molecular weight heparin, dextran sulfate and β-cyclodextrin tetradecasulfate, thrombin inhibitors such as hirudin, hirulog, PPACK (D-phe-L-propyl-L-arg-chloromethylketone) and argatroban, FXa inhibitors such as antistatin and TAP (tick anticoagulant peptide), Vitamin K inhibitors such as warfarin, as well as activated protein C;

(l) cyclooxygenase pathway inhibitors such as aspirin, ibuprofen, flurbiprofen, indomethacin and sulfinpyrazone;

(m) natural and synthetic corticosteroids such as dexamethasone, prednisolone, methprednisolone and hydrocortisone;

(n) lipoxygenase pathway inhibitors such as nordihydroguairetic acid and caffeic acid;

(o) leukotriene receptor antagonists; (p) antagonists of E- and P-selectins;

(q) inhibitors of VCAM-1 and ICAM-1 interactions;

(r) prostaglandins and analogs thereof including prostaglandins such as PGE1 and PGI2 and prostacyclin analogs such as ciprostene, epoprostenol, carbacyclin, iloprost and beraprost;

(s) macrophage activation preventers including bisphosphonates;

(t) HMG-CoA reductase inhibitors such as lovastatin, pravastatin, atorvastatin, fluvastatin, simvastatin and cerivastatin;

(u) fish oils and omega-3-fatty acids;

(v) free-radical scavengers/antioxidants such as probucol, vitamins C and E, ebselen, trans-retinoic acid, SOD (orgotein) and SOD mimics, verteporfin, rostaporfin, AGI 1067, and M 40419;

(w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives;

(x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518;

(y) cell motility inhibitors such as cytochalasin B;

(z) antiproliferative/antineoplastic agents including antimetabolites such as purine antagonists/analogs (e.g., 6-mercaptopurine and pro-drugs of 6-mercaptopurine such as azathioprine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin;

(aa) matrix deposition/organization pathway inhibitors such as halofuginone or other quinazolinone derivatives, pirfenidone and tranilast;

(bb) endothelialization facilitators such as VEGF and RGD peptide;

(cc) blood rheology modulators such as pentoxifylline and (dd) glucose cross-link breakers such as alagebrium chloride (ALT-711).

These therapeutic agents may be used individually or in combination, including in combination with any of the agents described herein.

Numerous additional therapeutic agents useful for the practice of the present invention are also disclosed in U.S. Pat. No. 5,733,925 to Kunz, the contents of which is incorporated herein by reference.

A wide range of therapeutic agent loadings may used in connection with the dosage forms of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

U.S. Pat. Nos. 5,833,632, 6,014,919, 6,260,458, and 6,428,489, 6,431,039 are hereby incorporated by reference herein. U.S. patent application Ser. No. 11/762,334 filed Jun. 13, 2007, is hereby incorporated by reference herein.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. An endoprosthesis holder comprising:
a proximal connector structure having an outer surface;
a distal connector structure having an outer surface;
an intermediate connector structure connected to said proximal connector structure and said distal connector structure such that said intermediate connector structure is between said proximal connector structure and said distal connector structure;
said intermediate connector structure comprising intermediate transverse structures and one or more axial structures, said intermediate transverse structures being connected to one another and to said proximal connector structure and to said distal connector structure by said one or more axial structures;
said intermediate connector structure having an outer surface; and
outward protrusions connected to said outer surfaces of said proximal connector structure, said distal connector structure, and said intermediate connector structure, wherein said one or more axial structures comprise at least two axial structures which are circumferentially offset relative to one another.

2. An endoprosthesis holder according to claim 1, wherein said proximal connector structure has a cross section which is annular such that said outer surface of said proximal connector structure is defined by an outer surface of said cross section of said proximal connector structure, said distal connector structure having a cross section which is annular such that said outer surface of said distal connector structure is defined by an outer surface of said cross section of said distal connector structure, said intermediate transverse structures having respective cross sections which are annular such that said outer surface of said intermediate connector structure is defined by outer surfaces of said cross sections of said intermediate transverse structures.

3. An endoprosthesis holder according to claim 1, wherein said proximal connector structure is integrally connected to said axial structures, said axial structures being integrally connected to said intermediate connector structures, said distal connector structure being integrally connected to said axial structures, said outward protrusions being integrally connected to said outer surfaces of said proximal connector structure, said distal connector structure, and said intermediate connector structure.

4. An endoprosthesis holder according to claim 1, wherein each of said intermediate transverse structures is connected to an adjacent one of said intermediate transverse structures or proximal connector structure or distal connector structure by a pair of said axial structures, each said pair of axial structures being connected to diametrically opposed locations of said intermediate connector structure.

5. An endoprosthesis holder according to claim 4, wherein each of said intermediate transverse structures has two of said pairs of said axial structures connected thereto such that one of said two of said pairs of said axial structures extends from said intermediate connector structure in an axial direction which is opposite from an axial direction in which said other of said two of said pairs of said axial structures extends from said intermediate connector structure, said axial structures each having respective axial centerlines, said two of said pairs of said axial structures being connected to said intermediate connector structures such that said axial centerlines of said one of said two of said pairs of said axial structures is circumferentially offset relative to said axial centerlines of said other of said two of said pairs of said axial structures.

6. An endoprosthesis holder according to claim 5, wherein said circumferential offset is 90 degrees.

7. An endoprosthesis holder according to claim 4, wherein said outward protrusions comprises a pair of axial outward protrusions each of which is connected to said outer surfaces of one of said pairs of said axial structures such that said outward protrusions are diametrically opposed relative to said intermediate connector structure.

8. An endoprosthesis holder according to claim 7, wherein said outward protrusions each have a transverse cross-section which is lobe-shaped.

9. An endoprosthesis holder according to claim 1, wherein said outward protrusions comprises a pair of outward protrusions which are connected to diametrically opposed locations of said outer surfaces of said proximal connector structure, said distal connector structure, and said intermediate connector structure.

10. A method for deploying a tubular stent contained within a delivery system having an endoprosthesis holder, the endoprosthesis holder having a proximal connector structure including an outer surface, the endoprosthesis holder further having a distal connector structure including an outer surface, the endoprosthesis holder further having an intermediate connector structure connected to the proximal connector structure and distal connector structure such that the intermediate connector structure is between the proximal connector structure and distal connector structure and in coaxial relation therewith, the intermediate connector structure comprising intermediate transverse structures and one or more axial structures, the intermediate transverse structures, being connected to one another and to the proximal connector structure and the distal connector structure by the axial structures, the intermediate connector structure having an outer surface, the endoprosthesis holder further having outward protrusions connected to the outer surfaces of the proximal connector structure, the distal connector structure, and the intermediate connector structure, wherein said one or more axial structures comprise at least two axial structures which are circumferentially offset relative to one another, the endoprosthesis holder being located within the tubular stent in coaxial relation therewith, the outward protrusions engaging the stent to resist displacement thereof relative to the endoprosthesis holder, the stent being located within a tubular sheath in coaxial relation therewith, said method comprising:

longitudinally retracting the sheath relative to the endoprosthesis holder, the engagement of the outward protrusions with the stent providing for said longitudinally retracting to uncover an axial portion of the stent which was previously covered by the sheath.

11. A method according to claim 10, and further comprising longitudinally displacing the sheath in a forward direction relative to the endoprosthesis holder, the engagement of the outward protrusions with the stent providing for said longitudinally displacing to cover an axial portion of the stent by the sheath for reconstraining the stent.

\* \* \* \* \*